US011396462B2

(12) United States Patent
Lust

(10) Patent No.: US 11,396,462 B2
(45) Date of Patent: *Jul. 26, 2022

(54) SYSTEMS AND METHODS FOR OZONE WATER GENERATION CELL WITH INTEGRATED DETECTION

(71) Applicant: NorthStar Medical Technologies, LLC, Beloit, WI (US)

(72) Inventor: Dorian Lust, Madison, WI (US)

(73) Assignee: Northstar Medical Technologies, LLC, Beloit, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/041,987

(22) PCT Filed: Mar. 29, 2019

(86) PCT No.: PCT/US2019/024881
§ 371 (c)(1),
(2) Date: Sep. 25, 2020

(87) PCT Pub. No.: WO2019/191614
PCT Pub. Date: Oct. 3, 2019

(65) Prior Publication Data
US 2021/0139350 A1  May 13, 2021

Related U.S. Application Data

(60) Provisional application No. 62/649,928, filed on Mar. 29, 2018.

(51) Int. Cl.
C02F 1/467 (2006.01)
C02F 1/461 (2006.01)
(Continued)

(52) U.S. Cl.
CPC .............. *C02F 1/4672* (2013.01); *C02F 1/20* (2013.01); *C02F 1/46109* (2013.01); *C25B 1/13* (2013.01);
(Continued)

(58) Field of Classification Search
CPC .................................. C25B 1/13; G01N 21/85
See application file for complete search history.

(56) References Cited

U.S. PATENT DOCUMENTS 6,287,431 B1  9/2001  Murphy et al.
6,391,183 B1  5/2002  Taniota et al.
(Continued)

FOREIGN PATENT DOCUMENTS

JP  2004324190 A  11/2004
JP  2008189969 A  *  8/2008
(Continued)

OTHER PUBLICATIONS

J. van den Broeke, et al "Use of on-line UV/Vis-spectrometry in the measurement of dissolved ozone and AOC concentrations in drinking water treatment" Water Science & Technology, 2008, p. 1169-1175. (Year: 2008).*

(Continued)

Primary Examiner — Brian W Cohen
(74) Attorney, Agent, or Firm — Husch Blackwell LLP

(57) ABSTRACT

A novel cell for generating ozonated water including an integrated ozone concentration detector. The cell comprises a nafion membrane separating a diamond coated anode, and a gold surfaced cathode enclosed within a cell housing with the catalyst side of the nafion membrane facing the cathode. The cell housing has a cathode housing portion and an anode housing portion separated by the membrane. The cathode and anode have an array of holes allowing fluid to penetrate to the surface of the niobium membrane. Ozonated water (Continued)

from the anode is channeled to a spectrophotometer integrated within the housing. The spectrophotometer creates a signal representative of the ozone concentration in the ozonated water which is utilized by control circuitry in a closed loop to maintain a stable target concentration. A bubble trap may be integrated within the housing through which the ozonated water passes before entering the spectrophotometer to remove bubbles form the ozonated water. Input ports allow fluid to flow into the housing and over the anode and cathode and then out of the housing through outlet ports.

20 Claims, 13 Drawing Sheets

(51) Int. Cl.
    *C25B 1/13* (2006.01)
    *C02F 1/20* (2006.01)
    *G01N 21/05* (2006.01)
    *C25B 9/19* (2021.01)
    *G01N 21/85* (2006.01)
    *G01N 21/25* (2006.01)
    *G01N 33/18* (2006.01)
    *C25B 9/65* (2021.01)

(52) U.S. Cl.
    CPC ............... *C25B 9/19* (2021.01); *C25B 9/65* (2021.01); *G01N 21/05* (2013.01); *G01N 21/25* (2013.01); *G01N 33/18* (2013.01); *C02F 2001/46142* (2013.01); *C02F 2001/46147* (2013.01); *C02F 2001/46157* (2013.01); *C02F 2201/46115* (2013.01); *C02F 2201/782* (2013.01); *C02F 2209/02* (2013.01); *C02F 2209/23* (2013.01); *G01N 21/85* (2013.01); *G01N 2201/062* (2013.01)

(56) References Cited

U.S. PATENT DOCUMENTS

| | | |
|---|---|---|
| 2003/0025909 A1* | 2/2003 | Hallstadius ............ G01N 21/33 356/436 |
| 2003/0121850 A1 | 7/2003 | Use et al. |
| 2007/0138401 A1 | 6/2007 | Tokhtuev et al. |
| 2009/0215110 A1 | 8/2009 | Gibson et al. |
| 2009/0219513 A1* | 9/2009 | Shakespeare ........ G01N 33/182 356/51 |
| 2012/0080379 A1 | 4/2012 | Zacharias |
| 2013/0032491 A1 | 2/2013 | Nitta et al. |
| 2016/0101997 A1* | 4/2016 | Hamaguchi ........... C02F 1/4672 204/252 |
| 2016/0347629 A1 | 12/2016 | Ceres et al. |

FOREIGN PATENT DOCUMENTS

| | | |
|---|---|---|
| JP | 2008189969 A | 8/2008 |
| JP | 5133592 B2 | 1/2013 |
| WO | 2011118917 A2 | 9/2011 |

OTHER PUBLICATIONS

Machine translation of JP2008-189969 of Nishimura. (Year: 2008).*
Basiriparsa, J. et al, "High-Efficiency Ozone Generation via Electrochemical Oxidation of Water Using Ti Anode Coated with Ni—Sb—SnO2," Journal of Solid State Electrochemistry, vol. 16, pp. 1011-1018 (2012).
Extended European Search Report re application No. EP 19776051. 5, dated Nov. 10, 2021.
Andersen, P.C. et al., "Miniature Personal Ozone Monitor Based on UV Absorbance," Analytical Chemistry, vol. 82, No. 19, pp. 7924-7928, Oct. 1, 2010; XP055640227 [Y] 1-5, 7-8 *; abstract; p. 2; p. 9, figure 1; p. 12, figure 4 * DOI: http://dx.doi.org/10.1021/ac1013578.

* cited by examiner

SYSTEMS AND METHODS FOR OZONE WATER GENERATION CELL WITH INTEGRATED DETECTION

RELATED APPLICATION

This application is a 371 of international application PCT/IB2019/024881 filed on Mar. 29, 2019 and claims priority to provisional application No. 62/649,928 filed Mar. 29, 2018 which are hereby incorporated herein by reference.

FIELD

The field relates to liquid ozone generating systems, and more particularly to an integrated cell for efficient, controlled generation of ozonated water.

BACKGROUND

Liquid oxidants such as ozonated water are widely used for cleaning and sterilization including water treatment, equipment sterilization, and food sterilization. Ozone is a strong oxidizer because its third oxygen atom can easily detach and bond with (i.e., oxidize) contaminants. Recent changes in sterile drug processing standards permit such a liquid phase ozone sterilant to be used as an alternative to heat and radiation. These cleaning and sterilization processes often require a controlled level of ozone concentration.

Known method of generating ozonated water use direct electrolysis wherein feed water is brought into direct contact with the electrolytic surface of a catalytic electrode to be electrolyzed into ozonated water. The catalytic electrode can include a cation exchange membrane, and an anode and a cathode in pressure contact with the cation exchange membrane on the respective surfaces. A feed-water supply path supplies water which comes into contact with the anode and the cation exchange membrane and the resulting ozonated water is then discharged through an ozonated water discharge path. These cleaning and sterilization processes often require a controlled level of ozone concentration.

These known devices for generating ozonated water are inefficient, inconsistent in performance and ozone concentration, often leak, and are expensive to fabricate and maintain. Thus, an improved ozonated water generation cell with integrated ozone detection is needed.

DETAILED DESCRIPTION

Figure 1:
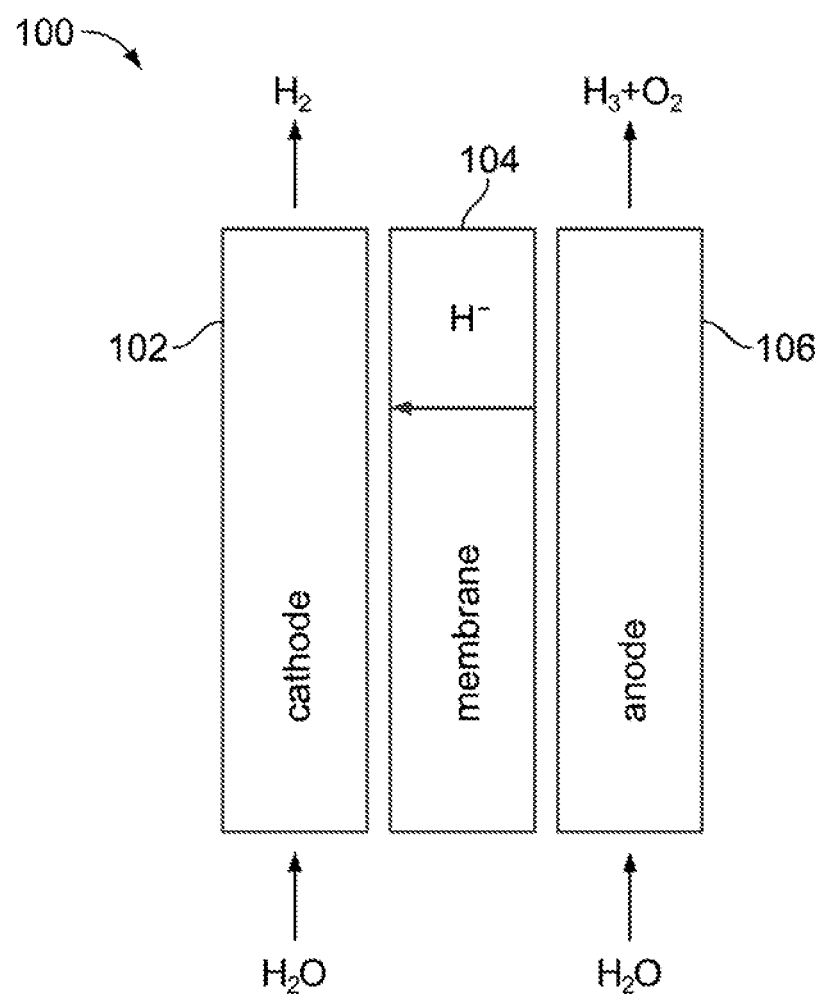
FIG. 1 is a block diagram of an example water ozonator cell, according to an example embodiment.

Example apparatus and methods for controlled ozonation of water are described herein. In the following detailed description of example embodiments of the invention, reference is made to the accompanying drawings that form a part hereof, and in which is shown by way of illustration specific example embodiments in which the invention may be practiced. These embodiments are described in sufficient detail to enable those skilled in the art to practice the inventive subject matter, and it is to be understood that other embodiments may be utilized and that logical, mechanical, electrical and other changes may be made without departing from the scope of the inventive subject matter.

Some portions of the detailed descriptions which follow are presented in terms of algorithms and symbolic representations of operations on data bits within a computer memory. These algorithmic descriptions and representations are the ways used by those skilled in the computer arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

In the Figures, the same reference number may be used to refer to an identical component that appears in multiple Figures. Signals and connections may be referred to by the same reference number or label, and the actual meaning will be clear from its use in the context of the description.

The description of the various embodiments is to be construed as examples only and does not describe every possible instance of the inventive subject matter. Numerous alternatives could be implemented, using combinations of current or future technologies, which would still fall within the scope of the claims. The following detailed description is, therefore, not to be taken in a limiting sense, and the scope of the inventive subject matter is defined only by the appended claims.

FIG. 1 is a block diagram of an example water ozonation cell 100. The cell 100 is an example in which a cathode 102 (e.g., stainless steel) is separated by a polymer membrane 104 (e.g. a nafion membrane) from an anode 106 (e.g. diamond plated niobium) as shown. In operation the cell 100 separates water into Hydrogen ($H_2$), and into oxygen in the form of $O_2$ and Ozone ($O_3$) by direct electrolysis using the polymer membrane 104. In this process, water is separated and independently introduced to the anode side of the electrolysis cell and to the cathode side of the cell. Water introduced in the anode side is electrolytically decomposed, a portion is converted to ozone, and mixes into the remaining water, thereby building the $O_3$ concentration in the water on the anode side. On the cathode side, the $H_2$ that has been separated and conveyed through the membrane is released into the water.

Advantages to producing ozone with such an electrolytic system are: 1) there is no ionic contamination because the feed-water is being disassociated using a solid hydrated ion exchange membrane; 2) the process water used for disinfection is the source of the oxygen for the generation of ozone—consequently, no outside contamination is introduced into the system being treated; and 3) the ozone is dissolved in the process water as soon as it is formed with no residual contaminants.

In the direct water electrolysis cell 100 of FIG. 1, ozone gas evolves at a voltage higher than 1.511 V, accompanied by oxygen evolution. By increasing voltage to above 2.075V, the oxidation of $O_2$ gas to form $O_3$ is also expected. Since $O_2$ evolution occurs at a lower potential than $O_3$ evolution, the production rate and electric power consumption in $O_2$ evolution are much higher than those in $O_3$ evolution. To ensure, therefore, that as much ozone as possible is produced, the anode should have an over potential above the decomposition and ozone reaction potential and the catalytic layer should inhibit the formation of diatomic oxygen and encourage the formation of ozone. This electrolysis cell design provides an efficient method of $O_3$ generation when the proper operating parameters are met. Parametric feedback may be utilized to ensure proper levels of ozone are produced in a given cell 100. A cell powered with a constant current source will have a resultant DC voltage which is in direct relation to ozone production and thus can be controlled to provide a consistent concentration of ozone. In some embodiments a desired concentration of 16 ppm of ozone can be achieved.

The cell's current density relationship to ozone generation is a factor of surface area and applied current. The current efficiency, and therefore ozone production, is stable at controlled water temperatures. In some embodiments a desired temperature between about 17° C. and 20° C. will provide a stable ozone concentration where the decay rate is matched by the generation rate. In the case of the cell 100, the constant flow rate of water, the maximum water temperature and the generation time will be factors in the stabilized ozone production concentration.

In conjunction with current and voltage, there are several other factors which affect ozone production. The factors are 1) fluid flow through the cell, 2) time of generation, 3) water pH and purification, 4) total water volume, and 5) water temperature. The cell 100 permits monitoring and regulating the above-mentioned five factors at a steady-state so as to significantly diminish the variable effects on ozone production. The fluid flow may be monitored and regulated to ensure it maintains a constant flow rate. The time of cell operation to generate ozone may be set to a defined duration. The water input is preferably USP sterile water which controls the pH and eliminates any contaminants. The input water volume may be monitored and controlled to ensure repeatable levels are sustained during the ozone generation cycle. The water temperature may be monitored and regulated to ensure it does not exceed a predetermined threshold.

Figure 2A:
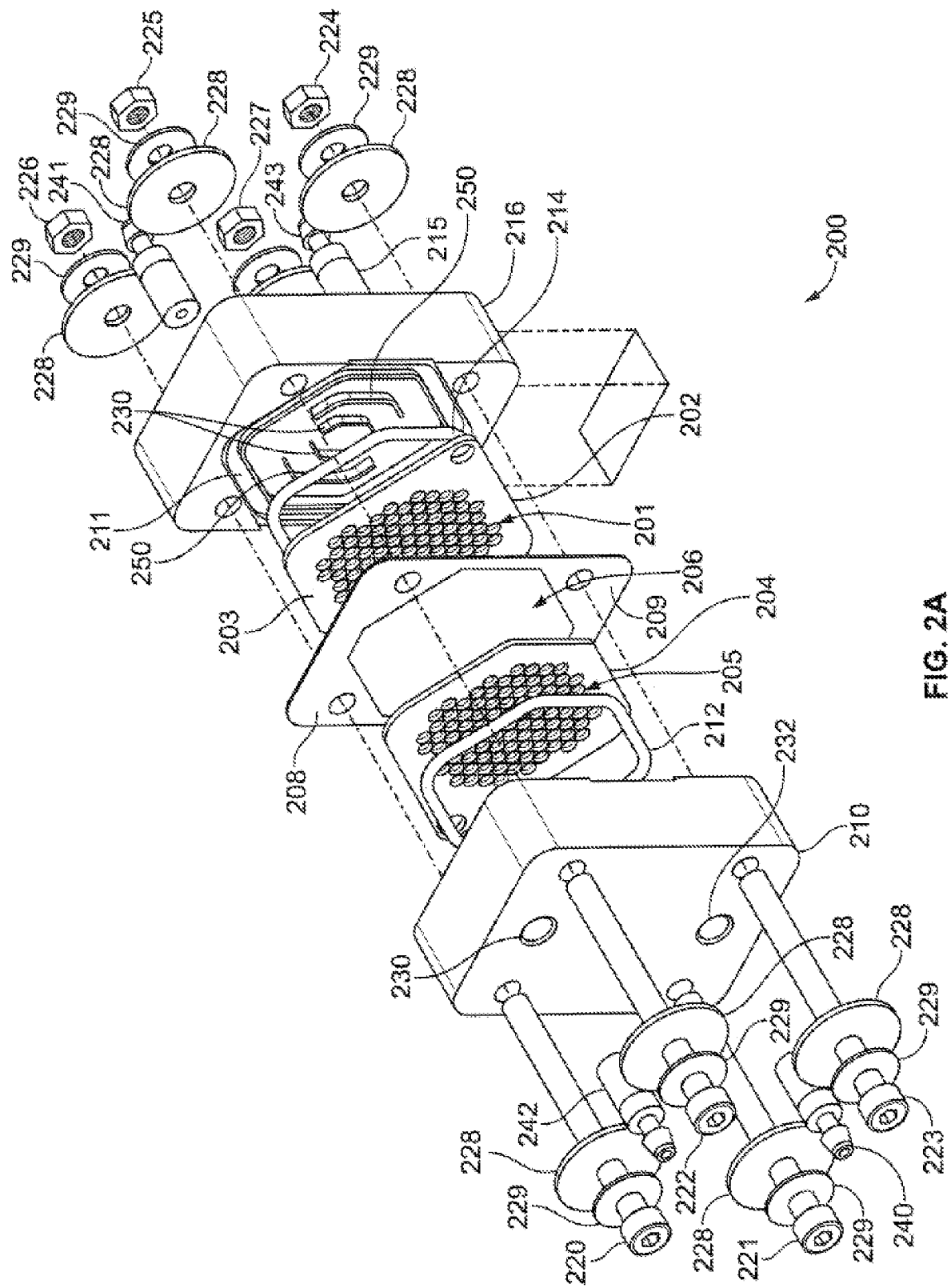
FIG. 2A is a an exploded view of an example ozonator cell device, according to an example embodiment.

FIG. 2A illustrates an exploded view of an embodiment of a novel ozonation cell 200 which is a specific example embodiment of the cell 100 of FIG. 1. The cell 200 comprises an anode 202 having a diamond coating on the side 203 facing a cathode 204 separated by a membrane 206. In the illustrated embodiment of FIG. 2A, both the anode 202 and the cathode 204 have an array of small holes 201, 205 that extend through the electrodes 202, 204. In one embodiment the anode 202 may be composed, for example, of niobium plated with a thin layer of doped diamond and the cathode 204 may be composed, for example, of stainless steel plated with gold.

The anode 202 may be any suitable conductor and is preferably niobium (or some other suitable material) coated with a layer of doped diamond. In one embodiment the niobium is about 99% pure and the diamond layer is about 2 microns thick. An array of holes 201 in the anode 202 allows water to contact the membrane 206 on the anode side while porosity of the membrane 206 allows the water to spread out between the holes of the array to wet the surface of the membrane 206 between the holes. The array of holes 201 of the anode 202 in one embodiment covers at least 75% of the surface area of the anode exposed to water (i.e., the area within the O-ring 214). In one embodiment the holes 201 are about 70 thousandths of an inch in diameter and should be large enough to allow water to adequately contact the membrane 206.

In some embodiments, the niobium anode surface is first anodized to create pores to promote surface adhesion, and then the doped diamond plating is applied. In other embodiments, the niobium surface may be bead blasted first and then etched to create an optimal surface texture to increase surface adhesion of the diamond plating In other approach, sputtering niobium onto the base material using a mask may be used to create surface texture to improve adhesion. In yet another embodiment the anode may be made of a thin mesh of niobium to maximize surface area, the mesh anode surface may then be prepared by any suitable method such as those described above which is then coated with a doped diamond layer. The diamond layer of the anode is preferably doped (i.e., doped with boron) to a concentration sufficient to make the diamond layer conductive. The diamond layer in some embodiments may be approximately two microns thick.

The cathode 204 is composed of a suitable conductor (e.g., stainless steel, gold, silver, etc.) which does not interact excessively with the fluid, preferably a gold surfaced electrode. In some embodiments the cathode 204 may be stainless steel plated on both sides with gold to create a gold surface to eliminate interaction of the water with iron. The cathode 204 also includes the array of holes 205 as shown. The array 205 in some embodiments covers at least 75% of the surface area of the cathode which is exposed to water (i.e., the area enclosed within the O-ring 212). The holes allow water iv contact the membrane 206 on the cathode side while porosity of the membrane 206 allows the water to spread out between the holes to wet the full surface covered by the array of holes 205 between the holes. In one embodiment the holes 205 are approximately 70 thousandths of one inch in diameter.

In the illustrated embodiment, the cathode 204 and anode 202 are separated by a polymer membrane 206, for example a nafion membrane. The membrane may contain a conductive diffuser oriented with the diffuser side 208 facing the cathode, as shown. The membrane may also contain a platinum catalyst on the side facing the cathode. In the illustrated embodiment an O-ring 212 (e.g. silicone) is located between the cathode 204 and a body element 210 to form a seal therewith, and a second O-ring 214 is located between the anode 202 and a second cell body element 216 to form a seal to minimize leakage of water from around the edge of the electrodes 204 and 206. In one embodiment, the membrane 206 is about 10 thousandths of an inch thick. The membrane 206 may absorb water so a double sided adhesive border 209 may be adhered to the membrane 206 to enhance the seal around the edges. A groove 211 may be formed in each body element 210, 216 to receive the O-rings.

In one embodiment, the body elements 210, 216 may be composed of ozone resistant high density polyethylene or CPVC. Four bolts 220-223 together with nuts 224-227 and washers 228,229 hold the body elements 210, 216 together to form an enclosure while holding the cathode 204, anode 202 and membrane 206 in place and properly aligned within the enclosure. Water inlet/outlet ports 230, 232 allow entry and exit of water to and from the cell 200. Water inlet/outlet adaptors 240, 242 are mounted to the ports 230, 232 to allow connection of water tubing. Ridges 250 may be formed in the inner surface of each body element 210, 216 to enhance the water flow pattern so that the water passes relatively evenly across the full face of the anode 203 and cathode 204 as it passes through the cell.

Figure 2C:
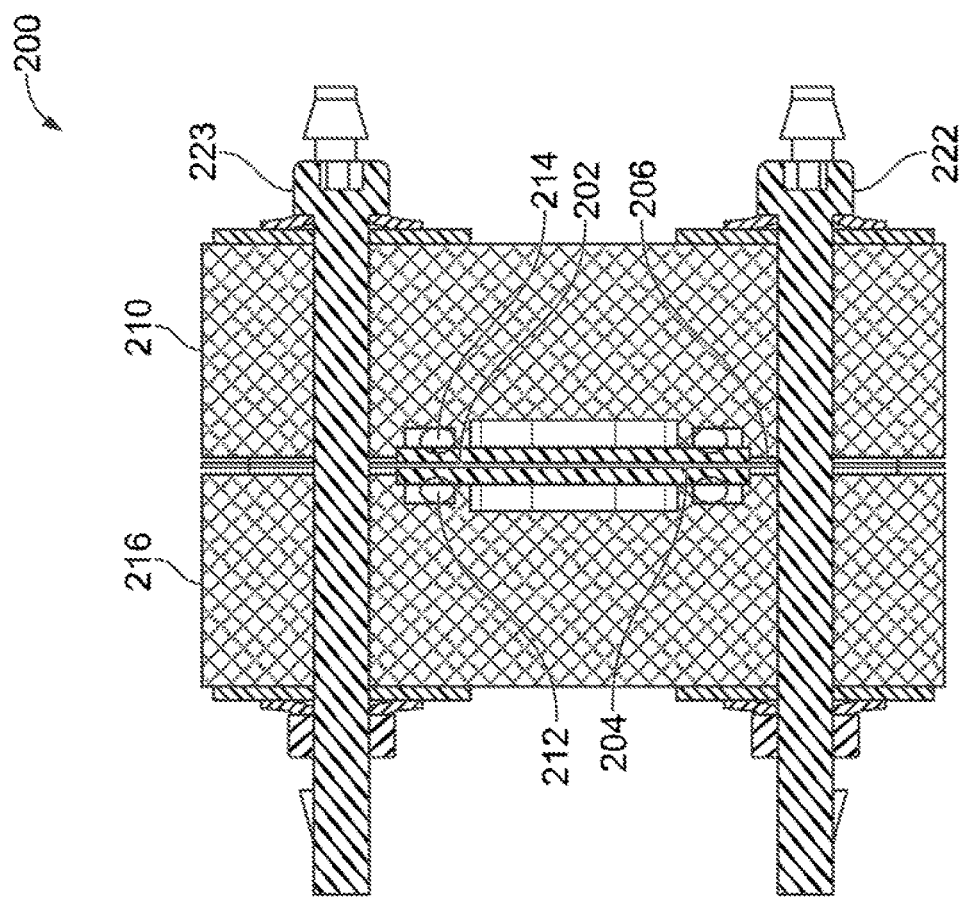
FIG. 2C is a cross-sectional view of the example of FIG. 2A.
Figure 2B:
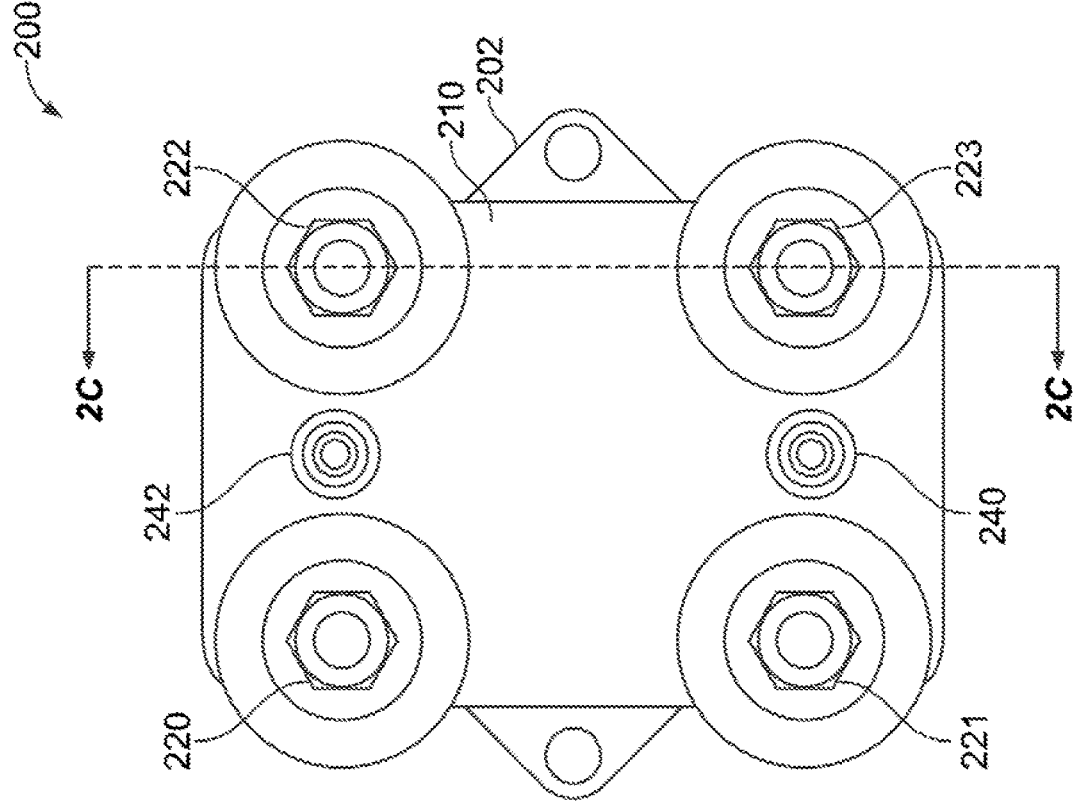
FIG. 2B is a side view of the example ozonator cell of FIG. 2A.

FIG. 2B illustrates an end view of the ozonation cell 200 with the bolts 220-223 and inlet/outlet adaptors 240, 242. FIG. 2C illustrate a cross-sectional view of the cell 200 along the line AA of FIG. 2B showing the body elements 210, 216 held together by the bolts 222, 223. Shown between the two body element 210, 216 are the O-ring 212, 214, the membrane 206, the cathode 204 and the anode 202. In some embodiments the bolts 220-223 are torqued to a desired level to control pressure on the electrodes. In one embodiment the bolts are torqued to approximately 6 ft-lbs to provide sufficient tightness while allowing water to flow on both sides contacting the nafion membrane 206 and to allow current to pass through the cell.

During operation of the cell 200, dc voltage is applied across the cell with the negative applied to the cathode and positive side to the anode. Water is pumped through the cell 200 entering the cathode side through the inlet port 232 to flow across the face of the cathode 204 and out of the cell 200 through the outlet port 230. The water is supplied via tubing connected to the outlet adapter 240, and flows out via tubing connected to the outlet adaptor 242. Similarly water enters the anode side of the cell 200 through the inlet port 215, from tubing connected to the inlet adapter 243, flows across the face of the anode 202 and out of the cell 200 via the outlet port and outlet adaptor 241. The water flowing on each side contacts the membrane 206 through the holes 201, 205. The water flow rate, water temperature, cell voltage and current are monitored and controlled to control the ozone concentration out of the cell 200.

In an alternative embodiment, the ozonation cell may include an integral spectral photometer to allow monitoring and control of ozone concentration. The spectral photometer portion projects UV light through the water flowing through a transparent chamber to measure ozone concentration. The integral spectral photometer also incorporates a bubble trap.

Figure 3:
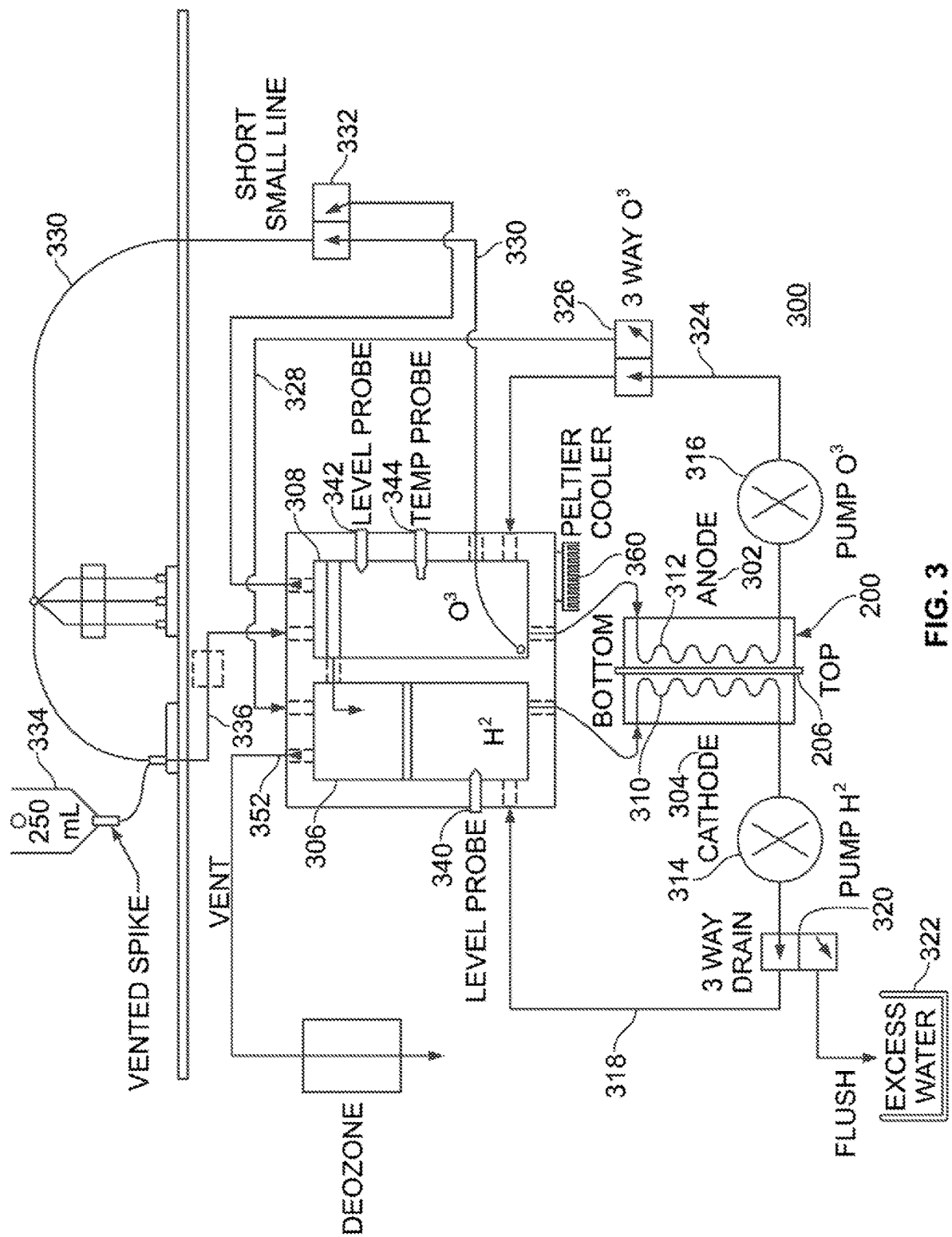
FIG. 3 is a functional diagram of an example system utilizing an ozonator cell.

FIG. 3 illustrates a functional diagram of an embodiment of an example water ozonation system 300, according to an example embodiment. The system 300 as shown includes an ozonation cell 200 having a cathode side 304, an anode side 302, and the membrane 206. The cell 200 is coupled to a pair of water reservoirs 306, 308 as shown. The reservoirs 306, 308 may be sized as needed, for example, in one embodiment, holding 50 ml and 200 mil, respectively. Fluid flows through the cell 200 via a cathode path 310 and an anode path 312. The fluid is driven through the cathode path 310 by a pump 314 which returns fluid with hydrogen to the hydrogen side reservoir 306 via a tubing path 318 through a three way valve 320 which can direct fluid into an excess fluid receptacle 322, as shown, to flush excess fluid. The fluid is pumped through the anode path 312 by a pump 316 via a tubing path 324 to the ozone reservoir 308 through a three way valve 326 which can also direct fluid to the reservoir 306 via a path 328, as shown. Also, in the illustrated embodiment, fluid can also be channeled from the bottom of the reservoir 308 via path 330 through a three way valve 332 to the top of the reservoir 308. A source of fluid is provided from a reservoir 334 to the reservoir 308 via a path 336. The reservoir 334 may be sized to hold a suitable amount for fluid, for example, in one embodiment, 250 ml of water. Levels in the reservoirs 306, 308 are monitored by level sensors 340, 342 and fluid temperature in the ozone reservoir 308 is monitored using temperature sensor 344. A cooler 350 (e.g. a Peltier cooler) permits control of fluid temperature in the reservoirs 308. A vent 352 provides a path for venting of excess gas from the reservoirs 306, 308.

Water from the ozone reservoir 308 is circulated to maintain a desired ozone level in the water while water is drawn out to be used for sterilization. The ozone concentration is controlled by controlling the voltage across the cell 200 and the current through the cell 200. A control board 400 (see FIG. 4) can monitor the cell 200 current and voltage and fluid temperatures to control ozone generation.

Figure 4:
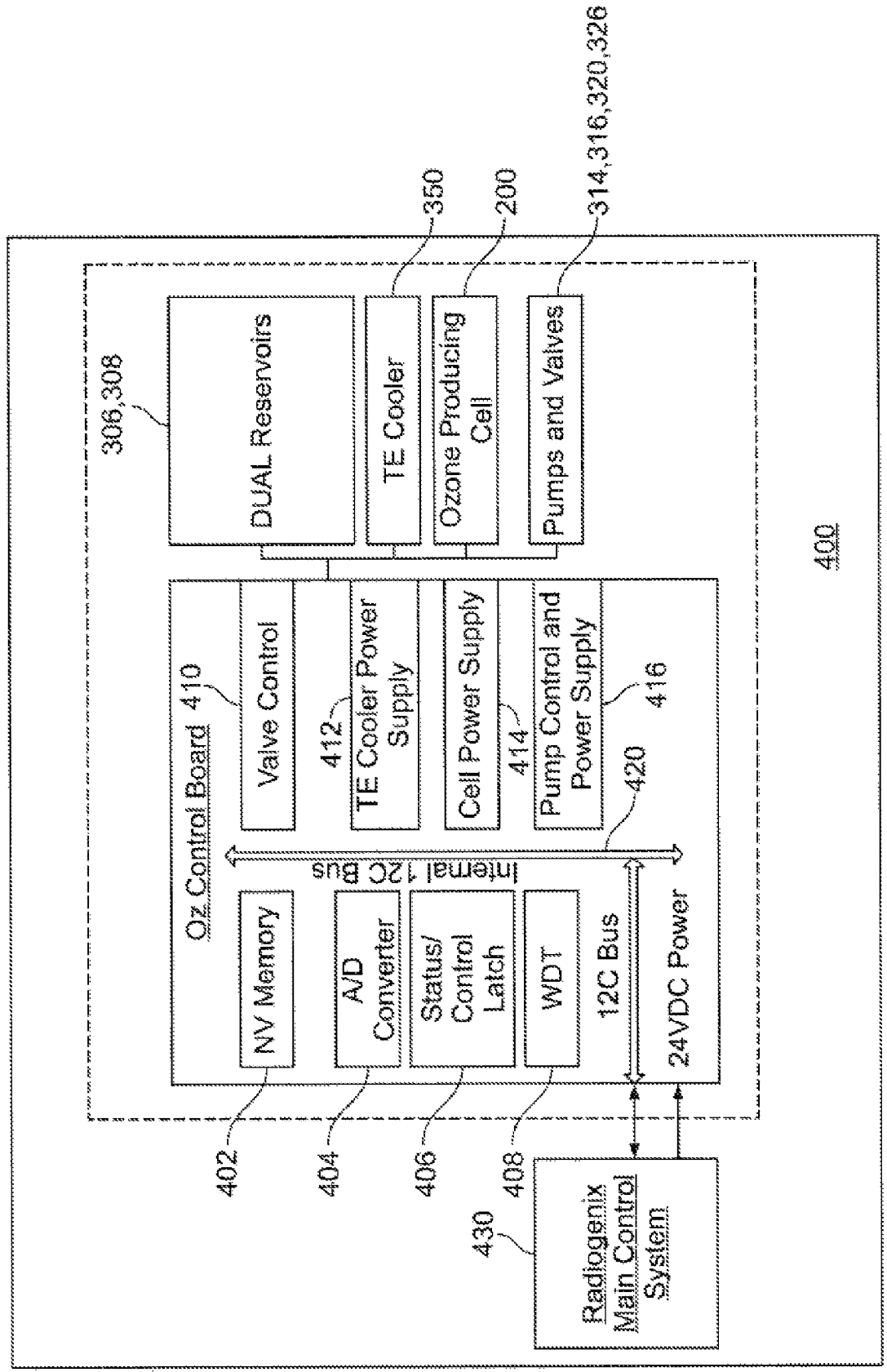
FIG. 4 is a functional block diagram of an example embodiment of control circuitry for the system of FIG. 3.

FIG. 4 illustrates a functional block diagram of an example of control circuitry 400 to control the exemplary embodiment of FIG. 3. The control circuitry 400 includes a memory 402, an A/D converter 404, control latch 406, WDT 408, valve control 410, cooler power supply 412, cell power supply 414 and pump control and power supply 416 communicating via a bus 420. The circuitry 400 is coupled, as illustrated to the reservoirs 306, 308 (i.e. to the sensors 340, 342, 344), to the cooler 350, and the cell 200. The control circuitry 400 is controlled by a controller 430 coupled via the bus 420.

Figure 5A:
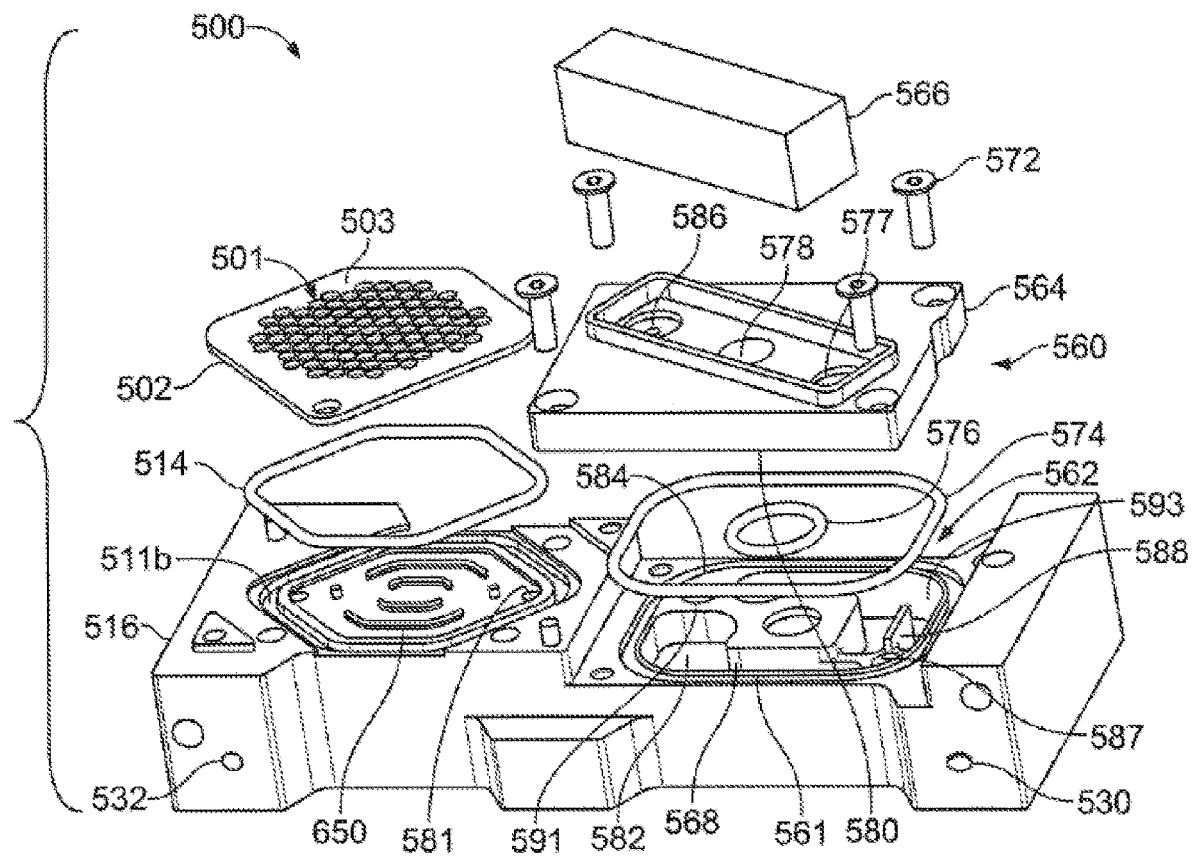
FIGS. 5A and 5B are an exploded view of an example ozonator cell having integrated spectrophotometer and bubble trap.
Figure 5B:
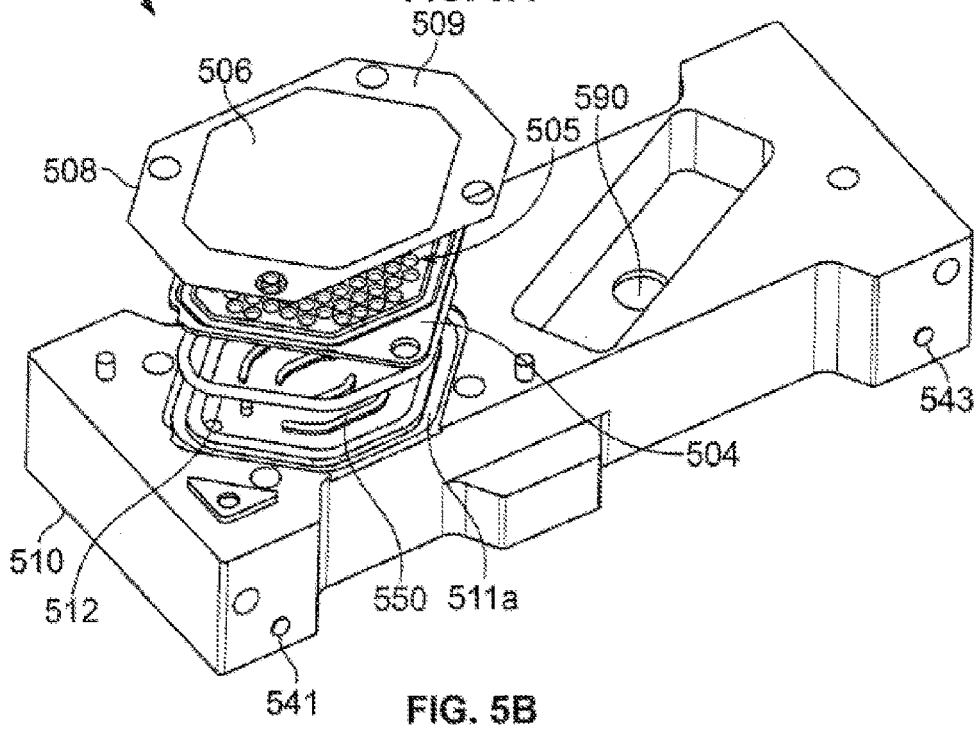

FIGS. 5A and 5B illustrate an exploded view of an embodiment of a novel ozonation cell 500 which is a specific example embodiment of the cell 100 of FIG. 1 with the addition of an integrated spectrophotometer and bubble trap. The cell 500 comprises two body elements 510 and 516. The cell 500 includes an ozonation cell similar to that of FIGS. 2A and 2B and comprises an anode 502 having a diamond coating on the side 503 facing a cathode 504 separated by a membrane 506. In the illustrated embodiment of FIGS. 5A and 5B, both the anode 502 and the cathode 504 have an array of small holes 501, 505 that extend through the electrodes 502, 504. In one embodiment the anode 502 may be composed, for example, of niobium plated with a thin layer of doped diamond and the cathode 504 may be composed, for example, of stainless steel plated with gold.

The anode 502 may be any suitable conductor and is preferably niobium (or some other suitable material) coated with a layer of doped diamond. In one embodiment the niobium is about 99% pure and the diamond layer is about 2 microns thick. An array of holes 501 in the anode 502 allows water to contact the membrane 506 on the anode side while porosity of the membrane 506 allows the water to spread out between the holes of the array to wet the surface of the membrane 506 between the holes. The array of holes 501 of the anode 502 in one embodiment covers at least 75% of the surface area of the anode exposed to water (i.e., the area within the O-ring 514). In one embodiment the holes 501 are about 70 thousandths of an inch in diameter and should be large enough to allow water to adequately contact the membrane 506.

In some embodiments, the niobium anode surface is first anodized to create pores to promote surface adhesion, and then the doped diamond plating is applied. In other embodiments, the niobium surface may be bead blasted first and then etched to create an optimal surface texture to increase surface adhesion of the diamond plating. In other approach, sputtering niobium onto the base material using a mask may be used to create surface texture to improve adhesion. In yet another embodiment the anode may be made of a thin mesh of niobium to maximize surface area, the mesh anode surface may then be prepared by any suitable method such as those described above which is then coated with a doped diamond layer. The diamond layer of the anode is preferably doped (i.e., doped with boron) to a concentration sufficient to make the diamond layer conductive. The diamond layer in some embodiments may be approximately two microns thick.

The cathode 504 is composed of a suitable conductor (e.g., stainless steel, gold, silver, etc.) which does not interact excessively with the fluid, preferably a gold surfaced electrode. In some embodiments the cathode 504 may be stainless steel plated on both sides with gold to create a gold surface to eliminate interaction of the water with iron. The cathode 504 also includes the array of holes 505 as shown. The array 505 in some embodiments covers at least 75% of the surface area of the cathode which is exposed to water (i.e., the area enclosed within the O-ring 512). The holes allow water to contact the membrane 506 on the cathode side while porosity of the membrane 506 allows the water to spread out between the holes to wet the full surface covered by the array of holes 505 between the holes. In one embodiment the holes 505 are approximately 70 thousandths of one inch in diameter.

In the illustrated embodiment, the cathode 504 and anode 502 are separated by a polymer membrane 506, for example a nafion membrane. The membrane may contain a conductive diffuser oriented with the diffuser side 508 facing the cathode, as shown. The membrane may also contain a platinum catalyst on the side facing the cathode. In the illustrated embodiment an O-ring 512 (e.g. silicone) is located between the cathode 504 and a body element 510 to form a seal therewith, and a second O-ring 514 is located between the anode 502 and a second cell body element 516 to form a seal to minimize leakage of water from around the edge of the electrodes 504 and 506. In one embodiment, the membrane 506 is about 10 thousandths of an inch thick. The membrane 506 may absorb water so a double sided adhesive border 509 may be adhered to the membrane 506 to enhance the seal around the edges. A groove 511a, 511b may be formed in each body element 510, 516 to receive the O-rings, as shown.

Figure 6A:
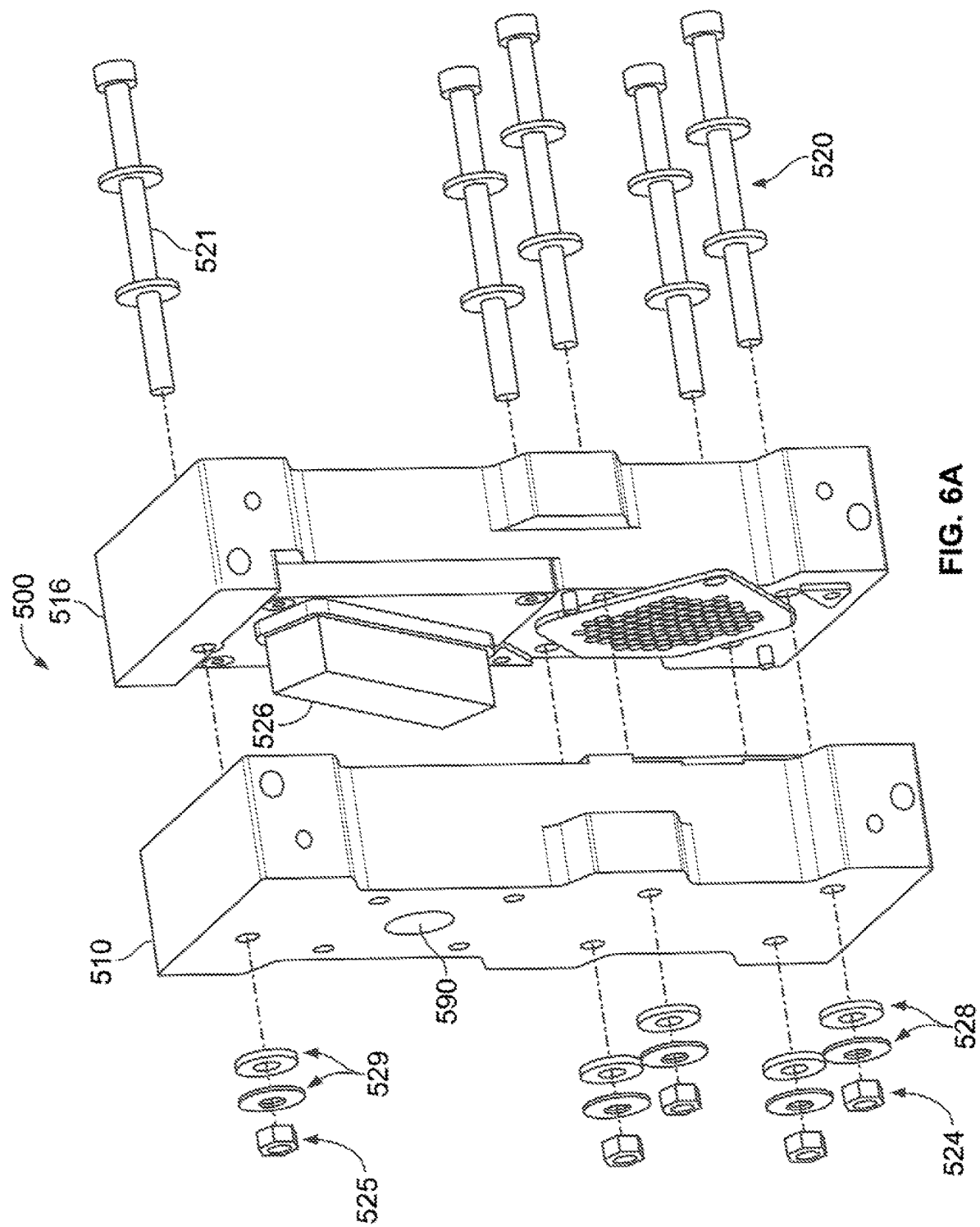
FIGS. 6A and 6B are exploded side views of an example of an assembled ozonator cell such as shown in FIGS. 5A and 5B.

In one embodiment, the body elements 510, 516 may be composed of ozone resistant high density polyethylene or CPVC. As shown in FIG. 6A, bolts 520, 521 together with nuts 524,525 and washers 528,529 hold the body elements 510,516 together to form an enclosure while holding the cathode 504, anode 502 and membrane 506 in place and properly aligned within the enclosure. This enclosure also houses a spectrophotometer 560 and a bubble trap 562 integrated within the enclosure. Water inlet/outlet ports 530,532 and ports 541 and 543 allow entry and exit of water to and from the cell 500. Ridges 550 may be formed in the inner surface of each body element 510, 516 to enhance the water flow pattern so that the water passes relatively evenly across the full face of the anode 503 and cathode 504 as it passes through the cell.

The illustrated embodiments of FIGS. 5A-5B include the integrated spectrophotometer 560 and the integrated bubble trap 562. The spectrophotometer 560 includes a cuvette 566 formed by a plate 564 and a transparent cuvette body 565. The cuvette body 565 is transparent to the light used in the spectrophotometer 560. In one embodiment the cuvette body 565 is made of quartz. The bubble trap 562 is formed by the body 516 having U-shaped channel 568 covered by the plate 564. The plate 564 is mounted on the body element 516 over channel 568 by a set of screws 572. An O-ring 574 forms a seal around the bubble trap channels 568 and the plate 564. Another O-ring 576 provides a seal around a central opening 578 in the plate 564 and an opening 580 through the body element 516. A groove 561 may be formed in the body elements 516 to receive the O-ring 574 to minimize a leakage.

Figure 5C:
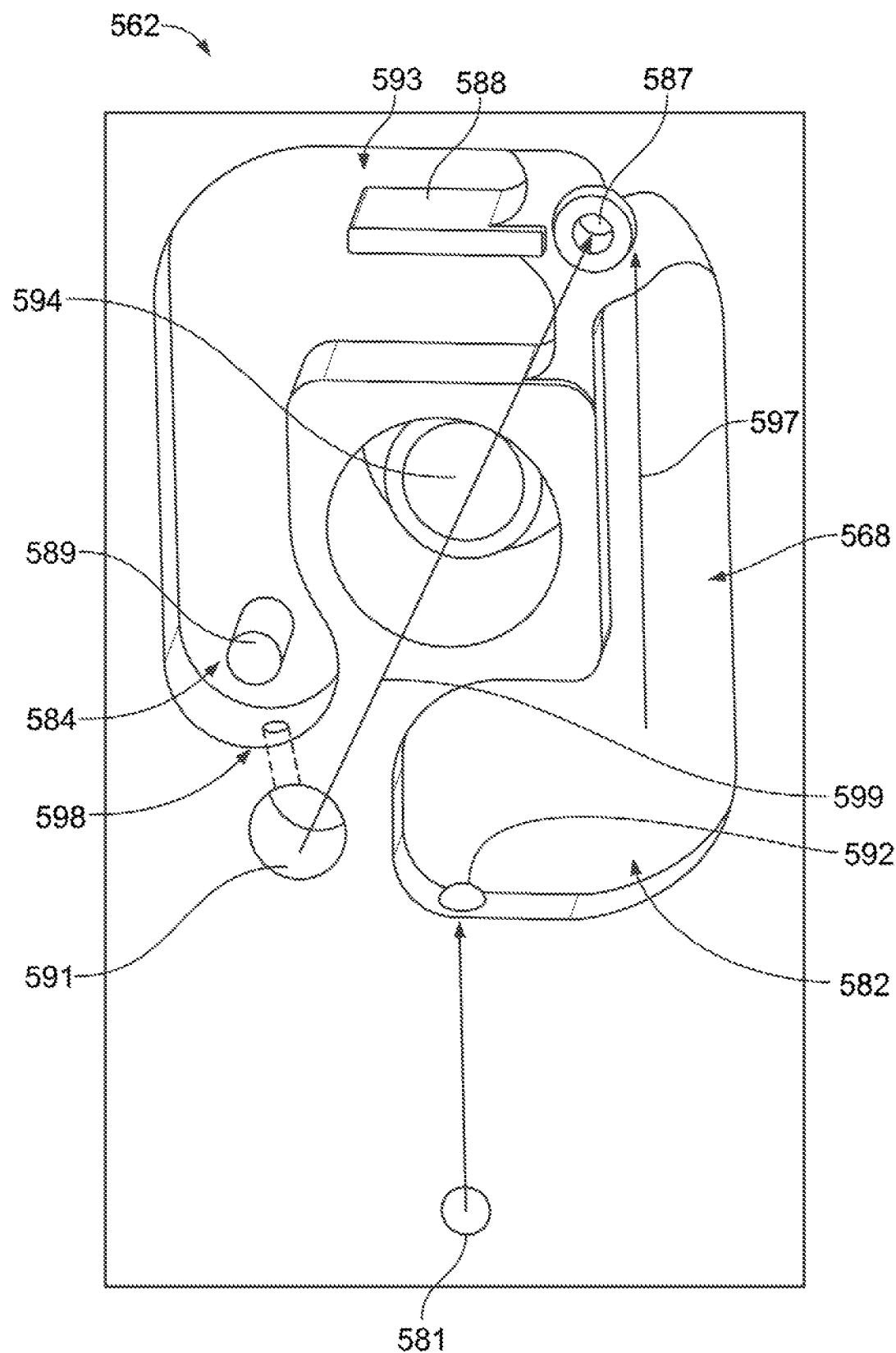
FIG. 5C is a diagrammatic illustration of an embodiment of the bubble trap of FIG. 5B.
Figure 6B:
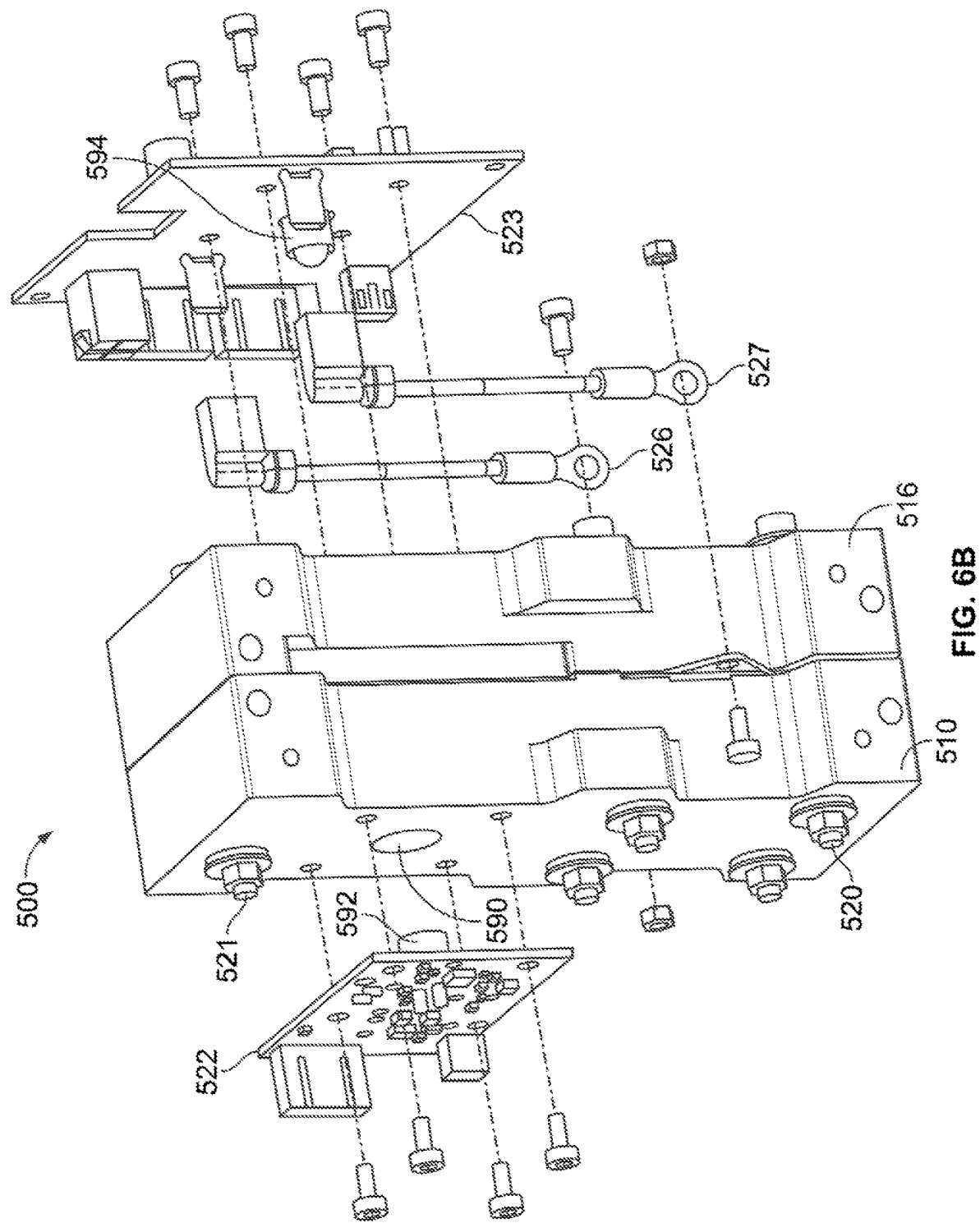

The functioning of the bubble trap 562 is described with reference to FIGS. 5A and 5C. During operation of the integrated cell 500, ozonated water flows from the anode via an opening 581 through a channel (not shown) in the body element 516 out of an opening 592 into a lower end 582 of the channel 568 of the bubble trap 562 where bubbles are removed from the ozonated water to prevent the bubbles from interfering with the functioning of the spectrophotometer 560. The illustrated embodiment of FIGS. 5A and 5B, 6A and 6B are typically mounted in a vertical position as illustrated in FIGS. 6A and 6B. This will result in the bubble trap vertically oriented with a lower end 582 of the channel and a top end 593. The ozonated water flows through the channel 568 toward the opening 587 near the top 593 of the channel 568, and a portion flows to the other end 584 of the channel 568, and then into the cuvette 566 through an orifice 598 and opening 591 and out of the cuvette 566 through a opening 587 to a channel (not shown) within the body element 516 to the outlet 530. While the ozonated water flows through the cuvette 564, light from a photodiode 594 is shined through the holes 578,580 through the water in the cuvette 564 and on to a photodetector 592 mounted outside of a hole 590. The photodiode 594 generates light of a frequency which is absorbed by ozonated water. In one embodiment a narrow band LED emitting a wavelength of 255 μm is used as the photodiode 594 with a matching photodetector 592. Ozone concentration of the water flowing through the cuvette is detected by the photodetector 592.

The bubble trap is desirable in order for the spectrophotometer 760 to function effectively because the spectrophotometer relies on a known volume of liquid that the UV light passes through. Bubbles in the liquid causes volume fluctuations which produce noise in resulting signal. The bubble trap 562 allows the majority of the water flow, as shown by the arrow 597 in FIG. 5C to pass up the channel 582 directly to the outlet port 530 carrying the bubbles out to the ozone reservoir where they rise to the surface and into the atmosphere. The trap uses a small side stream with an orifice 598 and flow baffles 588,589 that cause the liquid to slow. In one embodiment, the side stream is about 15% of the fluid and is slowed from about 1.5 inches/sec. to 0.3 inches/sec. This causes the bubbles to rise to and stay at the top 593 of the trap rather than flowing against gravity down to the orifice 598 at the bottom. The baffles 588,589 widen the flow and make it uniform to reduce high velocity regions that would pull bubbles down and the baffles 588 create some reverse flow across the top of the trap to help carry the bubbles into the opening 587 and to the outlet port 530. The portion of the water without the bubbles passes through the orifice 598 and out the opening 591 into the cuvette 566 where the UV light passes through it and is detected by the photodetector 592 to measure the ozone concentration. The water is pulled to the top when the liquid exiting the bubble trap creates a venturi that helps vacuum the liquid out of the cuvette 566 so it pass through the cuvette 566 to the opening 587 as shown by the arrow 599 in FIG. 5C, where it joins the rest of the fluid going to the outlet 530 and on to the ozone reservoir.

FIG. 6A illustrates a partially assembled end view of the ozonation cell 500 with the bolts 520,521 showing how the housing elements 510,516 are assembled. FIG. 6B illustrates an assembled view of the cell 500 showing the body elements 510, 516 held together by the bolts 520,521. Shown mounted to the two body element 510, 516 are control circuitry which controls operating of the cell 500 and the system, and which comprises circuit board 522 and circuit board 523. Circuit board 523 is mounted on the body element 516 as shown, and includes LED 594 which is aligned with the hole 580 to direct UV light through the cuvette 566. The circuit board 522 is mounted on the body element 510 and includes the photodetector 592 aligned with the hole 590 to detect the UV light that passes through the cuvette and the ozonated water within it to measure the ozone concentration of the water in the cuvette 566. Ozone concentration is determined by the amount of UV light that passes through the ozonated water because the higher the concentration of ozone the more the UV light is absorbed. Circuit board connector terminals 526, 527 connect the circuit board 523 to the cathode 504 and the anode 502. In one embodiment the bolts 520,521 are torqued to approximately 6 ft-lbs to provide sufficient tightness while allowing water to flow on both sides contacting the nafion membrane 206 and to allow current to pass through the cell.

During operation of the cell 500, dc voltage is applied across the cell with the negative applied to the cathode and positive side to the anode. As in cell 200 of FIG. 2A, water is pumped through the cell 500 entering the cathode side through the inlet port 532 to flow across the face of the cathode 504 and out of the cell 500 through the outlet port 530. Similarly water enters the anode side of the cell 500 through the inlet port 541 flows across the face of the anode 502 and out of the cell 500 via the outlet port 543. The water flowing on each side contacts the membrane 506 through the holes 501, 505. The water flow rate, water temperature, cell voltage and current are monitored and controlled to control the ozone concentration out of the cell 500.

Figure 7:
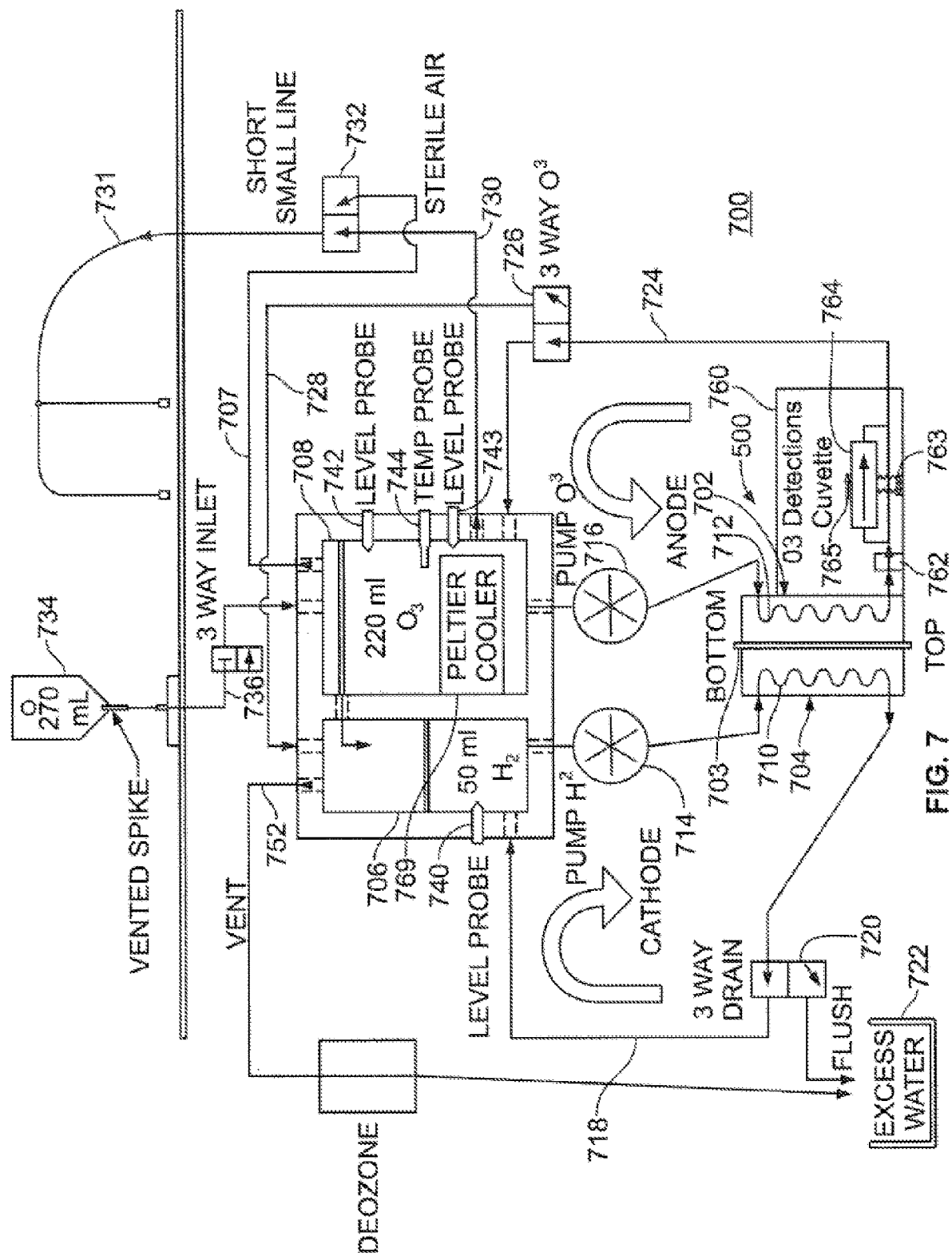
FIG. 7 is a functional diagram of an example system utilizing an ozonator cell having integrated spectrophotometer and bubble trap.

FIG. 7 illustrates a functional diagram of an example embodiment of a water ozonation system 700. The system 700 as shown includes an ozonation cell 500 (as shown in FIGS. 5A-6B) having a cathode side 704, an anode side 702, and a membrane 706. The cell 500 is coupled to a pair of water reservoirs 706,708 as shown. Fluid flows through the cell 500 via a cathode path 710 and an anode path 712. The fluid is driven through the cathode path 710 by a pump 714 which returns fluid with hydrogen to the hydrogen side reservoir 706 via a tubing path 718 through a three way valve 720 which can direct fluid into an excess fluid receptacle 722, as shown, to flush excess fluid. The fluid is pumped through the anode path 712 by a pump 716 via a tubing path 724 to a bubble trap 762 and through a cuvette 764 of a spectrophotometer 760 for ozone concentration detection and then to the ozone reservoir 708 through a three way valve 726 which can also direct fluid to the hydrogen reservoir 706 via a path 728, as shown. Fluid containing dissolved ozone is provided for use to an external system from the bottom of the ozone reservoir 708 via path 730 through the three way valve 732 and out on path 731. If sterile air is required as an output, it may be drawn from the top of the ozone reservoir 708 through the upper path 707 through the three way valve 732 and out path 731. A source of fluid is provided from a reservoir 734 to the reservoir 708 via a path 736. The reservoir 734 may be sized to hold a suitable amount for fluid, for example, in one embodiment, 250 ml of water. Levels in the reservoirs 706, 708 are monitored by level sensors 740, 742 and fluid temperature in the ozone reservoir 708 is monitored using temperature sensor 744. A cooler 750 (e.g. a Peltier cooler) permits control of fluid temperature in the reservoirs 708. A vent 752 provides a path for venting of excess gas from the reservoirs 706, 708.

Water from the ozone reservoir 708 is circulated to maintain a desired ozone level in the water while water is drawn out to be used for sterilization. The ozone concentration is controlled by controlling the voltage across the cell 500 and the current through the cell 500 in response to the detection of ozone concentration by the spectrophotometer 760. A control board 400 (see FIG. 4) can control the cell 500 current and voltage and fluid temperatures to control ozone generation.

Figure 8A:
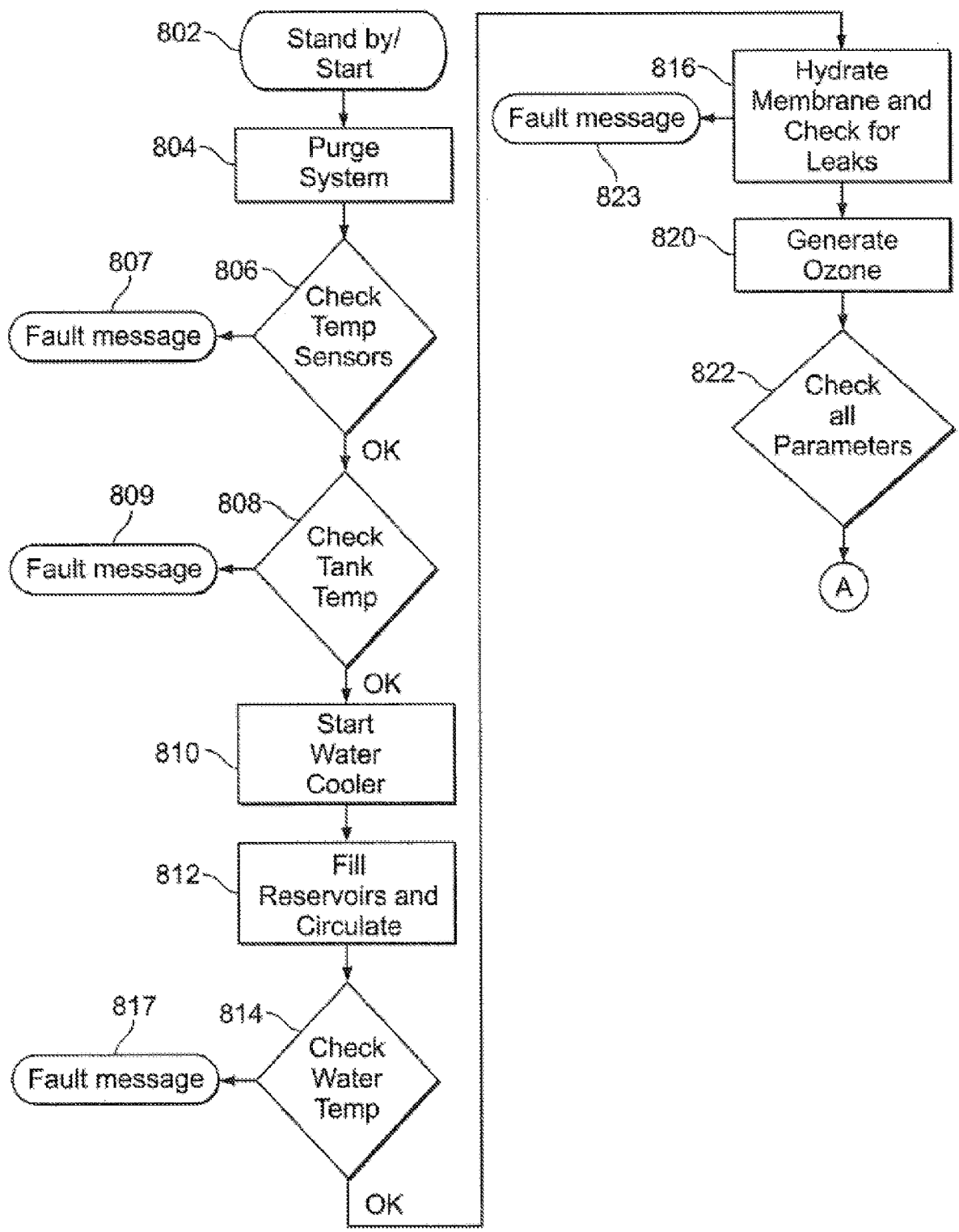
FIGS. 8A and 8B are flow diagrams of an example flow process for an embodiment of a ozone water generation system utilizing a ozonator cell having an integrated spectrophotometer and bubble trap.
Figure 8B:
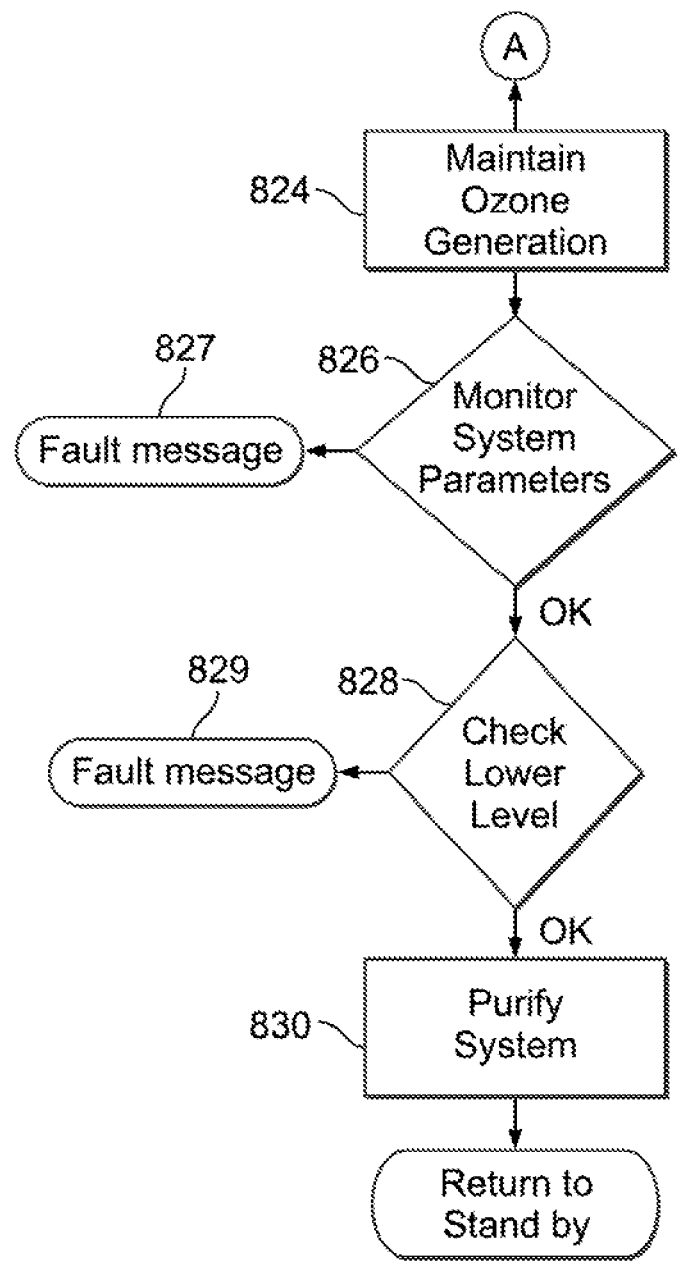
Figure 9:
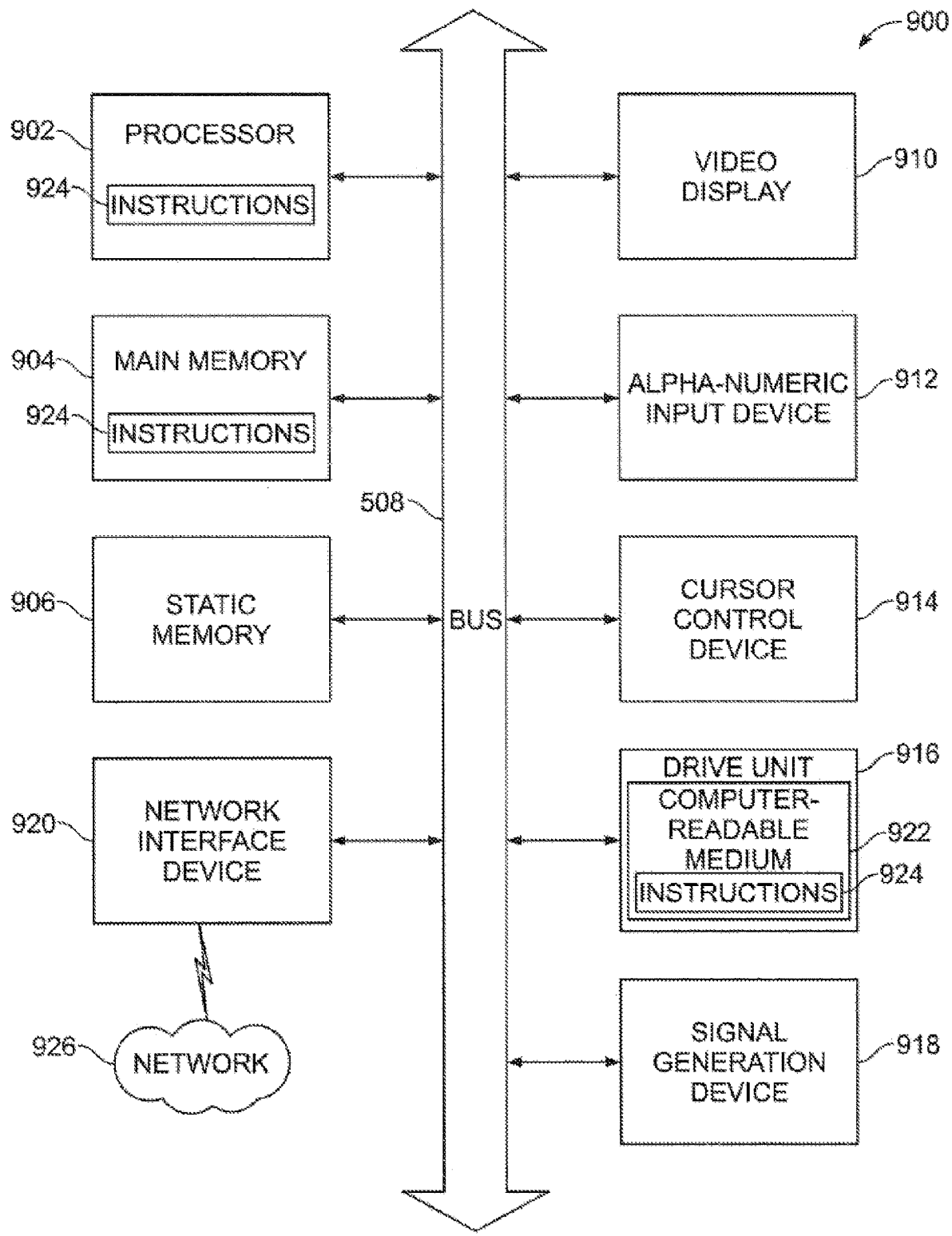
FIG. 9 is a block diagram of an example computer system within which a set of instructions for causing the machine to perform any one or more of the methodologies discussed herein may be executed or stored.

FIGS. 8A and B are flow diagrams of an example process for one complex cycle of an amount of ozonated water generation for an embodiment of the ozone generation system of FIG. 7 controlled by the control circuitry such as shown in FIGS. 4 and 9 and contained on circuit boards 522 and 523 as shown in FIG. 6B. The process starts at block 802 and a purge of the system is initiated as shown at block 804 during which circulation valves 720, 726 are opened and the pumps are run for a predetermined period of time (e.g., 75 seconds) to flush existing fluid out of the system. Next at block 806 a functionality check of the tank temperature sensor 744 and a board temperature sensor (not shown) is run, to determine if the sensors are operating properly within an acceptable temperature difference (e.g., ±12° C.), and then as shown at block 808 the tank temperature is checked without water to determine if it exceeds a desired threshold (e.g., 27° C.). A failure message may be generated if either test fails as illustrated at blocks 807,809. As illustrated at block 810, the water cooler 750 is started and a target temperature is set (e.g, 17.5° C.). Water is then allowed into the system 700 from water source 734 by opening the valve 736 to begin filling the reservoirs 706,708. After waiting for the water to rise to the ozone level sensor 742, the circulation pumps 714 and 716 are started and run for the predetermined time (e.g. 75 seconds) as illustrated at block 812. The water temperature is then checked to determine it is below a desired maximum (e.g., 20° C.) and a failure message may be generated if the maximum is exceeded as shown by block 814 815. If the water temperature is OK, then the membrane 703 is hydrated for a desired minimum time period, (e.g., 3 minutes) as illustrated by block 816 and level sensors are checked to ensure there are no leaks. If a leak is detected or no fluid detected a default message is generated as shown at block 817.

The cell 500 is then activated to generate ozone by targeting a predetermined ozone concentration (e.g., 20.5 ppm) as measured by the spectrophotometer 760 with closed loop control of the current as illustrated by block 820. All parameters are then checked as shown at block 822 to determine if all parameters are within acceptable limits and generate a fault message in not at block 823. In one embodiment the acceptable parameter ranges for the critical parameters may be a fluid temp of 13-24° C.; ambient temp of 13-40° C.; cell current of 0.1-1.5 Amp; cell voltage of 30-80 v; cell ppm of 16-24; pump rpm of 200-500 rpm; and pump current of 0.03-0.25 amp. Ozone generation may then be maintained as shown at block 824 by targeting an ozone concentration of 20.5 ppm with closed loop control of the cell current using the ozone concentration measurement output of the spectrophotometer 760. The valve 732 may be opened and ozonated water withdrawn to output line 731 during this time thereby providing for the external use of the ozonated water such as sterilization of medical equipment. Ongoing monitoring of the critical parameters of the system described above continues during operation as shown at block 826 with generation of a fault message if any parameter is out of the desired ranges at block 827 (e.g., fluid temp 13-24° C.; cell current; 0.1-1.5 amp; cell voltage 3.0-8.0 v; cell ppm 16-24; pump rpm 200-500 rpm; pump current 0.03-0.25 amp). As shown at block 828 the lower ozone tank liquid level sensor 743 is checked to determine that the tank no longer has liquid to thereby verify the end of a successful cycle (i.e., that the desired amount of ozonated water was withdrawn e.g., 250 ml), and a fault message is generated as indicated at block 829 to flag a unsuccessful cycle if the correct amount of fluid is not drawn out. When the cycle is completed, the crossover valve 726 is activated and ozonated water is pumped into the hydrogen tank for a predetermined time (e.g., 30 seconds) to clean the hydrogen tank, and then the crossover valve 726 is switched to circulate water in the system for a predetermined time (e.g., 30 seconds) to purge the system as shown at block 830. The system then returns to standby at block 802.

FIG. 9 shows a block diagram of an example embodiment of a machine in the form of a computer system 900 within which a set of instructions may be executed causing the system to perform any one or more of the methods, processes, operations, or methodologies discussed herein. The controller 430, for example, may include the functionality of the one or more computer systems 900.

The description of FIG. 9 is intended to provide a brief, general description of suitable computer hardware and a suitable computing environment in conjunction with which aspects of the invention may be implemented. In some embodiments, aspects of the inventive subject matter is described in the general context of computer-executable instructions being executed by a computer.

Those skilled in the art will appreciate that the aspects of the disclosure may be practiced with other computer system configurations, including hand-held devices, multiprocessor systems, microprocessor-based or programmable consumer electronics, smart phones, network PCs, minicomputers, mainframe computers, and the like. Aspects of the disclosure may also be practiced in distributed computer environments where tasks are performed by I/O remote processing devices that are linked through a communications network. In a distributed computing environment, program modules may be located in both local and remote memory storage devices.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, imbedded controller, a cellular telephone, a network router, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 may include a processor 902 (e.g., a central processing unit (CPU), a graphics processing unit (GPU) or both), a main memory 904 and a static memory 906, which communicate with each other via a bus 908. The computer system 900 further includes a video display unit 910 (e.g., a liquid crystal display (LCD) plasma, or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The disk drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media. The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, transitory and non-transitory media. Examples of non-transitory media include but are not limited to solid-state memories, optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

Such embodiments of the inventive subject matter may be referred to herein, individually or collectively, by the term "invention" merely for convenience and without intending to voluntarily limit the scope of this application to any single invention or inventive concept if more than one is, in fact, disclosed.

As is evident from the foregoing description, certain aspects of the inventive subject matter are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the inventive subject matter. Therefore, it is manifestly intended that this inventive subject matter be limited only by the following claims and equivalents thereof.

The methods described herein do not have to be executed in the order described, or in any particular order. Moreover, various activities described with respect to the methods identified herein can be executed in serial or parallel fashion.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A cell for ozonation of water comprising,
a cathode and an anode, separated by a membrane, the anode and cathode each have an array of holes to allow water to flow through to the membrane;
a housing enclosing the cell and having a cathode housing portion and an anode housing portion separated by the membrane, the cathode housing portion comprising a first inlet and a first outlet through which a first flow path is formed therebetween configured to allow water to flow across the cathode and the anode housing portion comprising a second inlet and a second outlet through which a second flow path is formed therebetween configured to allow water to flow across the anode to produce ozonated water flowing from the anode and further configured to allow at least some of the ozonated water from the second flow path to flow through an ozone concentration detector integrated within the housing and return to the second flow path, wherein the cathode housing portion encapsulates the cathode, the anode housing portion encapsulates the anode and the ozone concentration detector is a spectrophotometer; and
first and second input ports and first and second output ports are coupled to the first and second inlets and first and second outlets, respectively, of the housing to allow water to flow separately through both portions of the housing.

2. The cell of claim 1 wherein the ozone concentration detector is a spectrophotometer, wherein the spectrophotometer comprises a photodiode which directs light through a cuvette containing the ozonated water to a photodetector which detects the light that passes through the ozonated water in the cuvette.

3. The cell of claim 2 further comprising a bubble trap to remove bubbles from the ozonated water that flows through the ozone detector.

4. The cell of claim 1 wherein the cathode is made of stainless steel plated with gold, the anode is made of niobium plated on at least one side with a diamond layer doped with boron and the membrane is a nafion membrane.

5. The cell of claim 2 wherein the photodiode is a 255 nm LED and the photodetector is matched to the wavelength of the LED.

6. The cell of claim 2 wherein the cuvette is made of quartz.

7. A cell for ozonation of water comprising,
a cathode and an anode, separated by a membrane, the anode and cathode each have an array of holes to allow water to flow through to the membrane;
a housing enclosing the cell and having a cathode housing portion and an anode housing portion separated by the membrane, the cathode housing portion configured to allow water to flow across the cathode and the anode housing portion configured to allow water to flow across the anode to produce ozonated water flowing from the anode and configured to allow at least some of the ozonated water from the anode to flow through an ozone concentration detector integrated within the housing;
inlet and outlet ports coupled to the housing to allow water to flow separately through both portions of the housing; and
a bubble trap to remove bubbles from the ozonated water that flows through the ozone detector, wherein the bubble trap comprises a chamber including flow baffles which slow and widen flow of the ozonated water through the chamber and the ozone concentration detector is a spectrophotometer.

8. The cell of claim 7 wherein the bubble trap comprises a U-shaped chamber having a lower end and upper end and wherein the ozonated water flows into the lower end of a first side of the U-shaped channel from the anode, rises to an exit opening at the upper end where a portion of ozonated water flows down a second side of the U-shaped channel to an orifice which directs the portion to a first end of a cuvette of the spectrophotometer.

9. The cell of claim 1 further comprising ridges formed in an inner surface of the anode housing portion and the cathode housing portion to redirect water flow from the first and second inlets to the first and second outlets so that water passes evenly across the cathode and the anode.

10. The cell of claim 7 further comprising ridges formed in an inner surface of the anode housing portion and the cathode housing portion to redirect water flow from the inlets to the outlets so that water passes evenly across the cathode and the anode.

11. The cell of claim 1 wherein the array of holes do not cover the entire surface of the anode and the cathode.

12. The cell of claim 11 wherein the array of holes covers approximately 75% of the surface of the anode and the cathode.

13. The cell of claim 7 wherein the array of holes do not cover the entire surface of the anode and the cathode.

14. The cell of claim 13 wherein the array of holes covers approximately 75% of the surface of the anode and the cathode.

15. The cell of claim 7 wherein the ozone concentration detector is a spectrophotometer, wherein the spectrophotometer comprises a photodiode which directs light through a cuvette containing the ozonated water to a photodetector which detects the light that passes through the ozonated water in the cuvette.

16. The cell of claim 1 wherein the anode is a single part and the cathode is a single part.

17. The cell of claim 1 further comprising a double sided adhesive border adhered to the membrane.

18. The cell of claim 1 wherein the membrane includes a conductive diffuser.

19. The cell of claim 1 further comprising a first o-ring between the cathode housing portion and the cathode and a second o-ring between the anode housing portion and the anode.

20. The cell of claim 1 further comprising bolts through the cathode housing portion and the anode housing portion to hold the portions together, wherein the bolts are not through the cathode and the anode.

* * * * *